United States Patent
Newman et al.

(10) Patent No.: US 6,372,498 B2
(45) Date of Patent: *Apr. 16, 2002

(54) METHODS, SYSTEMS, AND KITS FOR INTRAVASCULAR NUCLEIC ACID DELIVERY

(75) Inventors: Christopher M. H. Newman, Sheffield (GB); Axel F. Brisken, Fremont, CA (US)

(73) Assignee: Pharmasonics, Inc., Sunnyvale, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/223,231

(22) Filed: Dec. 30, 1998

Related U.S. Application Data

(60) Provisional application No. 60/070,073, filed on Dec. 31, 1997.

(51) Int. Cl.[7] ............... C12N 12/63; A61M 1/00; A61N 1/30; A61K 48/00; A61B 17/20
(52) U.S. Cl. ............... 435/455; 604/19; 604/22; 604/28; 424/93.2; 424/93.21; 435/325; 536/23.1; 514/44
(58) Field of Search ............... 604/20, 21, 22, 604/28, 892.1, 105, 173, 306, 96; 514/44; 536/23.1; 424/93.21; 435/325, 455

(56) References Cited

U.S. PATENT DOCUMENTS

| | | | |
|---|---|---|---|
| 5,295,484 A | 3/1994 | Marcus et al. | |
| 5,328,470 A | * 7/1994 | Nabel et al. | 604/101 |
| 5,458,568 A | 10/1995 | Racchini et al. | 604/19 |
| 5,569,198 A | 10/1996 | Racchini | 604/96 |
| 5,586,982 A | 12/1996 | Abela | |
| 5,725,494 A | * 3/1998 | Brisken | 604/22 |
| 5,728,062 A | * 3/1998 | Brisken | 604/22 |
| 5,735,811 A | * 4/1998 | Brisken | 604/22 |
| 6,066,123 A | 5/2000 | Li et al. | 435/455 |

FOREIGN PATENT DOCUMENTS

| | | |
|---|---|---|
| WO | WO 90/11734 | 10/1990 |
| WO | WO 93/00052 | 1/1993 |
| WO | WO 95/25807 | 9/1995 |
| WO | WO 97/11720 | 4/1997 |
| WO | WO 97/12519 | 4/1997 |
| WO | WO 97/13849 | 4/1997 |
| WO | WO 97/40679 | 11/1997 |
| WO | WO 98/18391 | 5/1998 |
| WO | WO 99/21584 | 5/1999 |
| WO | WO 99/25385 | 5/1999 |

OTHER PUBLICATIONS

Boucher. J Clin Invest 1999 Feb.; 103:441–445.*

(List continued on next page.)

Primary Examiner—James Ketter
Assistant Examiner—Q Janice Li
(74) Attorney, Agent, or Firm—Townsend and Townsend and Crew LLP

(57) ABSTRACT

Nucleic acid transfection of vascular smooth muscle cells is enhanced by the application of vibrational energy to the cells. By applying vibrational energy at frequency in the range from 1 kHz to 10 MHz and at an intensity in the range from 0.01 W/cm$^2$ to 100 W/cm$^2$, significant enhancement of the uptake of nucleic acids into vascular smooth muscle cells can be achieved.

13 Claims, 7 Drawing Sheets

OTHER PUBLICATIONS

Miller et al. FASEB J 1995;9:190–99.*

Wyber et al. Pharma Res 1997 Jun.; 14:750–756.*

Bednarski et al., "In vivo target–specific delivery of macromolecular agents with MR–guided focused ultrasound" Radiology (1997) 204(1):263–268.

Sonoporator 100 ImaRx marketing literature, ImaRx, 1635 East 18$^{th}$ Street, Tucson, AZ, 85719, 2 pages total.

Baek et al., "Gene therapy for restenosis. Getting nearer to the heart of the matter" Circ. Res. (1998) 82:295–305.

Bao et al., "Transfection of a reporter plasmid into cultured cells by sonoporation in vitro"Ultrasound Med. Biol. (1997) 23:953–959.

Bauters et al., "The biology of restenosis" Prog. Cardiovasc. Dis. 91998) 40:107–116.

Bommannan et al., "Sonophoresis. I. The use of high–frequency ultrasound to enhance transdermal drug delivery" Pharmaceutical Research (1992) 9:559–564.

Feschheimer et al., "Measurement of cytoplasmic pH in dictyostelium discoideum by using a new method for introducing macromolecules into living cells" Eur. J. Cell. Biol. (1986) 40:242–247.

Gambihler et al., "Permeabilization of the plasma membrane of L1210 mouse leukemia cells using lithotripter shock waves" J. Membrane Biol. (1994) 141:267–275.

Gao et al., "Cationic liposome–mediated gene transfer" Gene Therap.(1995) 2:710–722.

Harrison et al., "In vitro mechanisms of chemopotentiation by tone–burst ultrasound" Ultrasound Med. Biol. (1996) 22(3):355–362.

He et al., "Application of ultrasound energy for intracardiac ablation of arrhythmias" Eur. Heart J. (1995) 16:961–966.

Kaufman et al., "Lysis and viability of cultured mammalian cells exposed to 1MHz ultrasound" Ultrasound Med. Biol. (1977) 3:21–25.

Kim et al., "Ultrasound–mediated transfection of mammalian cells" Hum. Gene Therap. (1996) 7:1339–1346.

Levy et al., "Effect of ultrasound on transdermal drug delivery to rats and guinea pigs" J. Clin. Invest. (1989) 83:2074–2078.

Pohl et al., "Effect of ultrasound on the steady–state transmembrane pH gradient and the permeability of acetic acid through bilayer lipd membranes" Biochem. Biophys. Acta (1993) 1145:279–283.

Tata et al., "Selective clinical ultrasound signals mediate differential gene transfer and expression in two human prostate cancer cell lines: LnCap and PC-3" Biochem. Bophys. Res. Comm. (1997) 234:64–67.

Tata et al., "Interaction of ultrasound and model membrane systems: Analysis and predications" J. Phys. Chem. (1992) 96:3548–3555.

* cited by examiner

METHODS, SYSTEMS, AND KITS FOR INTRAVASCULAR NUCLEIC ACID DELIVERY

This application is a continuation-in-part of provisional application Ser. No. 60/070,073, filed on Dec. 31, 1997, the full disclosure of which is incorporated herein by reference.

BACKGROUND OF THE INVENTION

1. Field of the Invention

The present invention relates generally to medical methods and devices. More particularly, the present invention relates to methods, systems, and kits for the delivery of nucleic acids to smooth muscle cells which line the lumen of blood vessels.

A number of percutaneous intravascular procedures have been developed for treating atherosclerotic disease in a patient's vasculature. The most successful of these treatments is percutaneous transluminal angioplasty (PTA) which employs a catheter having an expansible distal end, usually in the form of an inflatable balloon, to dilate a stenotic region in the vasculature to restore adequate blood flow beyond the stenosis. Other procedures for opening stenotic regions include directional atherectomy, rotational atherectomy, laser angioplasty, stents and the like. While these procedures, particularly PTA, have gained wide acceptance, they continue to suffer from the subsequent occurrence of restenosis.

Restenosis refers to the re-narrowing of an artery within weeks or months following an initially successful angioplasty or other primary treatment. Restenosis afflicts up to 50% of all angioplasty patients and results at least in part from smooth muscle cell proliferation in response to the injury caused by the primary treatment, generally referred to as "hyperplasia." Blood vessels in which significant restenosis occurs will require further treatment.

A number of strategies have been proposed to treat hyperplasia and reduce restenosis. Such strategies include prolonged balloon inflation, treatment of the blood vessel with a heated balloon, treatment of the blood vessel with radiation, the administration of anti-thrombotic drugs following the primary treatment, stenting of the region following the primary treatment, and the like. While enjoying different levels of success, no one of these procedures has proven to be entirely successful in treating all occurrences of restenosis and hyperplasia.

Of particular interest, it has recently been proposed to deliver nucleic acids to smooth muscle cells within blood vessels for the treatment of hyperplasia and other disease conditions. See, e.g. U.S. Pat. No. 5,328,470. Progress in vascular gene therapy, however, has been hindered by the limited efficiency and/or toxicity of most currently available transfection materials and techniques. Current methods used to achieve nucleic acid transfer into vascular smooth muscle cells comprise the delivery of naked DNA, cationic liposomes, and specialized adenoviral and retroviral vectors. Each of these approaches are problematic. While the use of adenoviral vectors can achieve relatively high transfection efficiencies, the use of viruses raises concern among many experts in the field.

For these reasons, it would be desirable to provide additional and/or improved methods, systems, kits, and the like for the delivery of nucleic acids to vascular smooth muscle cells and other cells which comprise the vascular wall. It would be particularly desirable if such gene delivery methods were useful for the treatment of hyperplasia in regions of a blood vessel which have previously been treated by angioplasty, atherectomy, stenting, and other primary or secondary treatment modalities for atherosclerotic disease. Such methods should provide efficient gene delivery, result in minimum necrosis of the cells lining the vasculature (particularly smooth muscle cells and endothelial cells), permit targeting of vascular smooth muscle cells, be capable of being performed with relatively simple catheters and other equipment, and suffer from minimum side effects. At least some of these objectives will be met by the invention described hereinafter.

2. Description of the Background Art

Catheters and methods for intravascular transfections are described in U.S. Pat. No. 5,328,470 and published in PCT applications WO 97/12519; WO 97/11720; WO 95/25807; WO 93/00052; and WO 90/11734.

Ultrasound-mediated cellular transfection is described or suggested in Kim et al. (1996) Hum. Gene Ther. 7:1339–1346; Tata et al. (1997) Biochem. Biophy. Res. Comm. 234:64–67; and Bao et al. (1997) Ultrasound in Med. & Biol. 23:953–959. The effects of ultrasound energy on cell wall permeability and drug delivery are described in Harrison et al. (1996) Ultrasound Med. Biol. 22:355–362; Gao et al. (1995) Gene Ther. 2:710–722; Pohl et al. (1993) Biochem. Biophys. Acta. 1145:279–283; Gambihler et al. (1994) J. Membrane Biol. 141:267–275; Bommannan et al. (1992) Pharma. Res. 9:559–564; Tata and Dunn (1992) J. Phys. Chem. 96:3548–3555; Levy et al. (1989) J. Clin. Invest. 83:2074–2078; Feschheimer et al. (1986) Eur. J. Cell Biol. 40:242–247; and Kaufinan et al. (1977) Ultrasound Med. Biol. 3:21–25. A device and method for transfection, endothelial cells suitable for seeding vascular prostheses are described in WO 97/13849.

Local gene delivery for the treatment of restenosis following intravascular intervention is discussed in Bauters and Isner (1998) Progr. Cardiovasc. Dis. 40:107–116 and in Baek and March (1998) Circ. Res. 82:295–305.

A high frequency ultrasonic catheter employing an air-backed transducer which may be suitable for performing certain methods according to the present invention is described in He et al. (1995) Eur. Heart J. 16:961–966. Other catheters suitable for performing at least some methods according to the present invention are described in co-pending application Ser. Nos. 08/565,575; 08/566,740; 08/566,739; 08/708,589; 08/867,007, and 09/223,225, assigned to the assignee of the present invention, the full disclosures of which are incorporated herein by reference.

SUMMARY OF THE INVENTION

The present invention comprises methods, systems, and kits for the delivery of nucleic acids to the smooth muscle cells of the type which line coronary arteries and other blood vessels. The delivery of nucleic acids to target cells is generally referred to as "transfection," and the transfection methods of the present invention are advantageous since they are capable of significantly increasing transfection efficiency, i.e. the amount of nucleic acid materials taken up by the smooth muscle cells to which they are delivered. The methods of the present invention are useful with a wide variety of nucleic acid types. For example, it has been found that significant transfection efficiencies can be obtained even with naked DNA and RNA molecules i.e., nucleic acids which are not incorporated into liposomes, viral vehicles, plasmids, or other conventional nucleic acid vehicles. The methods are not limited to such naked nucleic acids, however, they are also suitable for the delivery of nucleic acids incorporated into liposomes and other vesicles; viral vectors, including both adenoviral vectors and retroviral vectors; plasmids, and the like.

The methods of the present invention are particularly suitable for delivering nucleic acids incorporated into liposomes often referred to as "lipofection," to the vascular smooth muscle cells. As is demonstrated in the Experimental section hereinafter, transfection of vascular smooth muscle cells with naked DNA is enhanced significantly by vibratory energy (by a factor of 7.5 in the particular data shown), but overall transfection efficiency still remains at a relatively low level. In contrast, lipofection enhanced with vibratory energy according to the present invention shows a lesser enhancement over lipofection without vibrational energy (by a factor of three in the particular data which are shown), but the overall transfection efficiency, is substantially greater than that which can be achieved with naked nucleic acids, even with vibrational energy enhancement. Thus, the combination of lipofection with vibrational energy enhancement will frequently be preferred. While similar overall transfection efficiencies may be achieved with vibrational enhancement of viral vectors, the use of viral vectors will often not be preferred because of the safety concerns which have been raised with respect to such delivery vehicles. Additionally, as other delivery vehicles are developed as alternatives for variations of the liposome and viral vehicles which presently find use, it will be expected that the vibratory enhancements of the present invention will find use with such methods. A significant advantage of the present invention, however, is that such delivery vehicles are not essential for efficient uptake.

While the methods, systems, and kits of the present invention will preferably be used with in vivo transfection techniques described above, they will also find use with in vitro techniques for transfecting vascular smooth muscle cells in culture. Such in vitro methods will find use in many contexts, such as in the testing of different structural and regulatory genes to determine their effect on vascular smooth muscle cells, the transformation of vascular smooth muscle cells to other predictable phenotypes research purposes, and the like. In other instances, it may be desirable to transfect autologous or heterologous vascular smooth muscle cells in vitro so that the cells can later be "seeded" back into a patient for a particular therapeutic purpose. For example, vascular smooth muscle cells can be transfected to produce therapeutic proteins which can be released by the transfected cells after they are implanted or otherwise introduced to a patient.

The nucleic acids may be in the form of genes, gene fragments, sense oligonucleotides and polynucleotides, antisense oligonucleotides and polynucleotides, and any other type of nucleic acid having biological activity or benefit. Exemplary genes that may be delivered for treating cardiovascular disease and hyperplasia include angiogenic factors, such as vascular endothelial growth factor (VEGF), endothelial nitric oxide synthase (eNOS), tissue inhibitor matrix matallio-proteinase (TIMP), p21, and the like.

Smooth muscle and other vascular cells are transfected according to the present invention by delivering nucleic acids to the cells located, for example, in a target region within a blood vessel or in cell culture. The cells are exposed to vibratory energy at a frequency and intensity selected to enhance the uptake of the nucleic acids by the smooth muscle cells, which line the blood vessel wall. The exposure of the cells to the vibratory energy can occur before exposure or introduction of the nucleic acids, after exposure or introduction of the nucleic acids, or simultaneously with such exposure or introduction. Preferably, exposure of the cells to the vibratory energy will continue for at least a time (total elapsed time) following the introduction or exposure of the cells to the nucleic acids, typically for at least 10 seconds, preferably for at least 60 seconds, more preferably for at least 300 seconds, and still more preferably for at least 900 seconds, usually being in the range from 10 seconds to 900 seconds.

Preferably, the vibratory energy is delivered at a frequency in the range from 1 kHz to 10 MHz, preferably in the range from 20 kHz to 3 MHz, usually from 100 kHz to 2 MHz. The intensity of the vibrational energy will usually be in the range from 20 W/cm$^2$ to 100 W/cm$^2$, preferably in the range from 0.1 W/cm$^2$ to 10 W/cm$^2$, usually from 0.5 W/cm$^2$ to 5 W/cm$^2$. The vibratory energy may be delivered continuously during the transfection event, or alternatively may be delivered intermittently, e.g. with a duty cycle within the range from 1% to 100%, usually from 5% to 95%, preferably from 10% to 50%.

The duration of exposure of the cells to the vibration energy will be a function of total elapsed time (usually within the range and limits set forth above), the duty cycle (percentage of the total elapsed time in which the vibrational energy is turned on), and pulse repetition frequency (PRF; the frequency at which the vibrational energy is turned off and on, typically in the range from 1 Hz to 1000 Hz). Generally, the duty cycle and/or PRF can be controlled to permit heat dissipation to maintain a temperature in the treated artery or cell culture below 45° C., preferably below 42° C., and more preferably below 40° C. Higher temperatures can be deleterious to the viability of the vascular smooth muscle cells.

The vibrational energy will usually be ultrasonic energy and may be delivered in a variety of ways. For example, the vibrational energy may be delivered from an external source, e.g. by focused ultrasonic systems, such as high intensity focused ultrasound (HIFU) systems which are commercially available. Usually, however, the ultrasonic energy will be delivered intravascularly using an interface surface which is disposed within the region within the blood vessel. The interface surface is vibrationally excited to radiate ultrasonic energy directly or indirectly (as defined below) into the blood vessel wall. Typically, the ultrasonic surface is carried on a flexible catheter having a vibrational transducer or other oscillator disposed on the catheter near the surface. The transducer is then energized to vibrate the surface within the desired frequency range and at the desired intensity. Alternatively, ultrasonic or other vibrational energy can be delivered from an external source down a transmission member through the catheter to the interface surface. For in vitro methods, a variety of hand-held probes and transducers could be employed. A particular transducer useful for imparting vibratory energy to cultures of vascular smooth muscle cells is described in the Experimental section hereinafter.

The vibrational energy may be delivered directly into the blood vessel wall, e.g. by contacting the interface surface directly against a portion of the wall within the target region. Alternatively, the vibrational energy can be delivered indirectly by vibrating the surface within blood or other liquid medium within the blood vessel. Usually, the nucleic acids will be released or disposed in the liquid medium. In an exemplary embodiment, the nucleic acids are contained within a suitable transfection medium which is localized within the target region by a pair of axially spaced-apart balloons. The interface surface is also disposed between the balloons, and energy is applied to the entrapped medium via the interface surface. Alternatively, the nucleic acid medium may be delivered to the interior of a porous balloon and/or to fluid delivery conduits secured to the outside of a balloon, where in both cases the vibrational transducer can be mounted on the catheter body within the balloon. Conveniently, the medium containing the nucleic acids can be delivered to the region via the same catheter, optionally being recirculated or replenished via the catheter during the treatment.

Alternatively, the nucleic acids can be delivered to the patient systemically while the vibrational energy is applied locally and/or from an external source as described above.

Optionally, the nucleic acids may be delivered to a vascular target site in the presence of microbubbles of gas or other cavitation nucleation components. It is believed that low intensity vibration of the type preferably employed in the methods of the present invention will generally not induce cavitation in a vascular environment devoid of cavitation nucleii. As cavitation is presently believed to contribute to the formation of pores in the walls of the smooth muscle cells (and thus enhance nucleic acid uptake), the introduction of microbubbles or other cavitation nucleii together with the nucleic acids, e.g. from the same delivery catheter, may significantly enhance the nucleic acid uptake. For example, the nucleic acids may be delivered in a liquid medium to which dissolved gases have been added as cavitation nucleii.

The nucleic acids can be delivered to the smooth muscle or other vascular cells for a variety of purposes. In a preferred example, the nucleic acids are delivered to a region of the blood vessel which has previously been treated by a primary intravascular technique for treating cardiovascular disease, such as balloon angioplasty, directional atherectomy, rotational atherectomy, stenting, or the like. The methods of the present invention for inhibiting intimal hyperplasia in vascular smooth muscle cells will find particular use following stenting procedures in order to prevent or inhibit hyperplasia which can occur following stenting. The nucleic acids delivered will be intended to inhibit hyperplasia and/or promote angiogenesis following such primary treatment. Methods for promoting angiogenesis, of course, need not be performed in conjunction with a primary treatment. Suitable genes for such treatments have been described above.

Kits according to the present invention will comprise a catheter having an interface surface which may be vibrated. The kits will further include instructions for use setting forth a method as described above. Optionally, the kits will further include packaging suitable for containing the catheter and the instructions for use. Exemplary containers include pouches, trays, boxes, tubes, and the like. The instructions for use may be provided on a separate sheet of paper or other medium. Optionally, the instructions may be printed in whole or in part on the packaging. Usually, at least the catheter will be provided in a sterilized condition. Other kit components, such as the nucleic acids to be delivered, may also be included.

Systems according the present invention will comprise a catheter having an interface surface which may be vibrated at the frequencies and power levels described above. Such systems may further include nucleic acids in a form suitable for the transfection or lipofection of vascular smooth muscle cells lining an artery or other blood vessel. The nucleic acids may be naked, viral-associated, but will preferably be incorporated within liposome vesicles in order to enhance transfection efficiency when delivered in the presence of vibratory energy according to the methods of the present invention. The catheter will usually be packaged in a sterile tray, pouch, or other conventional container, while the nucleic acid reagent will be incorporated in an ampoule, bottle, or other conventional liquid pharmaceutical container. Optionally, the catheter and reagent will be packaged together in a box, bag, or other suitable package. Further optionally, the systems may include instructions for use as described above.

BRIEF DESCRIPTION OF THE DRAWINGS

(FIGS. 7 and 8). Parallel adherent cell counts were performed at baseline (time 0) and at 3, 18 and 48 h after transfection (FIGS. 9 and 10). Where applicable ultrasonic energy (1 MHz, CW, 0.4 W/cm$^2$, 60 s) was applied for 30 minutes into the 3 h transfection period. Asterisks indicate significant differences between control and ultrasound-exposed cells ($p<0.05$).

DESCRIPTION OF THE SPECIFIC EMBODIMENTS

Figure 1:
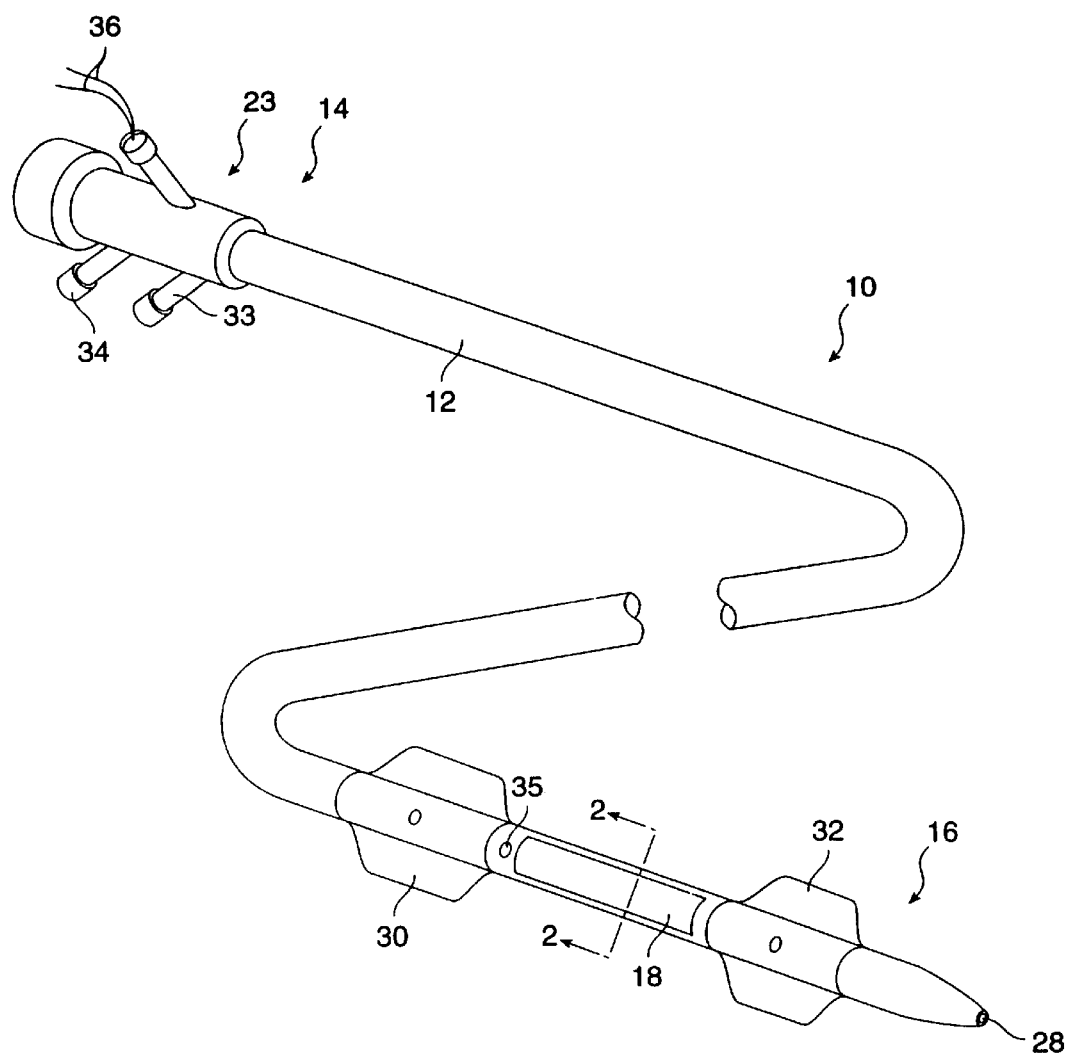
FIG. 1 is a perspective view of a catheter suitable for use in the methods of the present invention.

The nucleic acids delivered by the methods and devices of the present invention will comprise nucleic acid molecules in a form suitable for uptake into target cells within a host tissue, usually smooth muscle cells lining the blood vessels. The nucleic acids will usually be in the form of bare DNA or RNA molecules, where the molecules may comprise one or more structural genes, one or more regulatory genes, antisense strands, strands capable of triplex formation, or the like. Commonly, such nucleic acid constructs will include at least one structural gene under the transcriptional and translational control of a suitable regulatory region. Optionally, but not necessarily, the nucleic acids may be incorporated in a viral, plasmid, or liposome vesicle delivery vehicle to improve transfection efficiency.

If viral delivery vehicles are employed, they may comprise viral vectors, such as retroviruses, adenoviruses, and adeno-associated viruses, which have been inactivated to prevent self-replication but which maintain the native viral ability to bind a target host cell, deliver genetic material into the cytoplasm of the target host cell, and promote expression of structural or other genes which have been incorporated in the particle. Suitable retrovirus vectors for mediated gene transfer are described in Kahn et al. (1992) CIRC. RES. 71:1508–1517, the disclosure of which is incorporated herein by reference. A suitable adenovirus gene delivery is described in Rosenfeld et al. (1991) SCIENCE 252:431–434, the disclosure of which is incorporated herein by reference. Both retroviral and adenovirus delivery systems are described in Friedman (1989) SCIENCE 244:1275–1281, the disclosure of which is also incorporated herein by reference.

The nucleic acids may preferably be present in a lipid delivery vehicle which enhances delivery of the genes to target smooth muscle cells within the vascular epithelia or elsewhere. Transfection in a lipid delivery vehicle is often referred to as "lipofection." Such delivery vesicles may be in the form of a liposome where an outer lipid bilayer surrounds and encapsulates the nucleic acid materials. Alternatively, the nucleic complexes may be in the form of a nucleic acid-lipid dispersion, nucleic acid-lipid emulsion, or other combination. In particular, the complexes may comprise liposomal transfection vesicles, including both anionic and cationic liposomal constructs. The use of anionic liposomes requires that the nucleic acids be entrapped within the liposome. Cationic liposomes do not require nucleic acid entrapment and instead may be formed by simple mixing of the nucleic acids and liposomes. The cationic liposomes avidly bind to the negatively charged nucleic acid molecules, including both DNA and RNA, to yield complexes which give reasonable transfection efficiency in many cell types. See, Farhood et al. (1992) BIOCHEM. BIOPHYS. ACTA. 1111:239–246, the disclosure of which is incorporated herein by reference. A particularly preferred material for forming liposomal vesicles is lipofection which is composed of an equimolar mixture of dioleylphosphatidyl ethanolamine (DOPE) and dioleyloxypropyl-triethylammonium (DOTMA), as described in Felgner and Ringold (1989) NATURE 337:387–388, the disclosure of which is incorporated herein by reference.

It is also possible to combine these two types of delivery systems. For example, Kahn et al. (1992), supra., teaches that a retrovirus vector may be combined in a cationic DEAE-dextran vesicle to further enhance transformation efficiency. It is also possible to incorporate nuclear proteins into viral and/or liposomal delivery vesicles to even further improve transfection efficiencies. See, Kaneda et al. (1989) SCIENCE 243:375–378, the disclosure of which is incorporated herein by reference.

The nucleic acids will usually be incorporated into a suitable carrier to facilitate delivery and release, into the blood vessels according to the present invention. The carriers will usually be liquids or low viscosity gels, where the nucleic acids will be dissolved, suspended, or otherwise combined in the carrier so that the combination may be delivered through the catheter and/or carried by the catheter and released intravascularly at the treatment site. Alternatively, the nucleic acids may be provided in a dry or solid form and coated onto or otherwise carried by the catheter or the vibrational surface.

Figure 2:
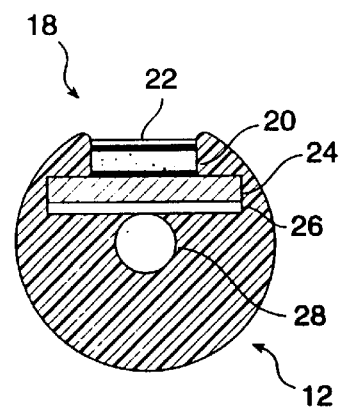
FIG. 2 is a cross-sectional view taken along line 2—2 of FIG. 1.

An exemplary catheter 10 suitable for use in the methods of the present invention is illustrated in FIGS. 1 and 2. The catheter 10 comprises a catheter body 12 having a proximal end 14, a distal end 16, and a vibrational interface surface 18 near the distal end. The vibrational interface surface 18 comprises a piezoelectric ceramic 20 disposed between an insulating layer 22 and an aluminum shim 24. An air gap 26 is behind the shim, and the transducer assembly is suitable for a high frequency oscillation. The catheter further includes a central lumen 28 to enable the catheter to be delivered over a guidewire in a conventional manner. The catheter further includes a pair of axially spaced-apart balloons 30 and 32 on either side of the vibrational interface surface 18. The balloons 30 and 32 may be inflated via an inflation port 33 on a proximal hub 23 secured to the proximal end 14 of the catheter body 12. The proximal hub also includes an infusion port 34 which can deliver an infusate, usually comprising the nucleic acids to be delivered, through a port 35 between balloons 30 and 32 and proximate the vibrational interface surface 18. The hub further includes wires 36 which permit the transducer 24 to be connected to a suitable driver, e.g. a commercially available signal generator and power amplifier capable of exciting the transducer within the target frequency ranges and intensities.

Figure 3:
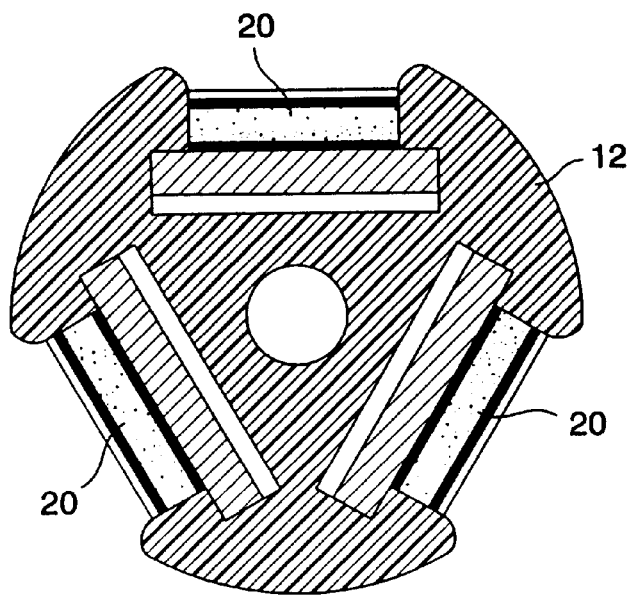
FIGS. 3 and 4 are alternative cross-sectional views for the catheter of FIG. 1.
Figure 4:
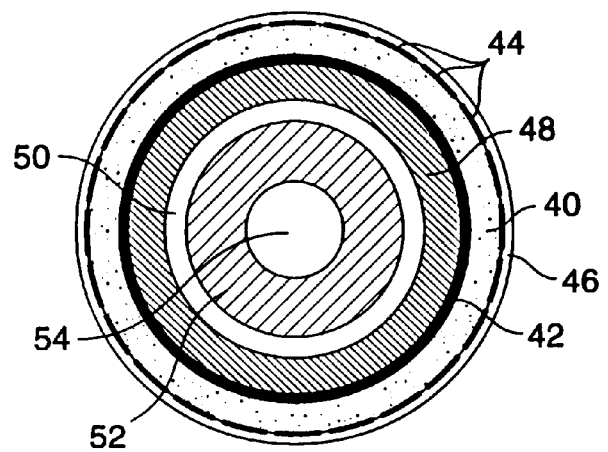

While a single transducer 24 is illustrated in FIGS. 1 and 2, it will frequently be desirable to provide multiple transducers 20, as illustrated in FIG. 3, or a circularly symmetric transducer 40, as illustrated in FIG. 4. As illustrated in FIG. 3, a plurality of transducers 20 could be circumferentially spaced-apart about the exterior of the catheter body 12. In this way, energy can be transmitted radially outwardly in multiple directions at once. In order to enhance the uniformity of the treatment, the catheter could optionally be rotated while the energy is being delivered. In order to further enhance the uniformity of ultrasonic energy being radiated outwardly, the multiple transducer embodiments can be driven by a multiplexd power source. To still further enhance the uniformity of ultrasonic energy being delivered, a piezoelectric transducer 40 can be formed in a cylindrical geometry, as illustrated in FIG. 4. The transducer ceramic 40 can be driven by inner and outer electrodes 42 and 44, and the outer electrodes coated by a thin insulating layer 46. A transducer ceramic can be supported on a suitable cylinder, such as an aluminum cylinder 48, and for high frequency operation an air gap 50 may be provided. The transducer can be mounted symmetrically about catheter body 52 having a conventional guidewire lumen 54. In all of the above cases, the dimensions will depend in large part on the frequency of operation as well as the catheter size. The width of the transducers will typically be in the range from 0.1 mm to 6 mm, usually from 0.5 mm to 3 mm. The length of the transducer may vary from 1 mm to 2 or more cm, with the length being primarily limited by loss of flexibility of the distal end of the catheter. Multiple transducer elements could also be provided along the length of the catheter, i.e. being axially spaced-apart. Other transducer designs may be employed, such as those disclosed in the copending applications cited above.

Figure 5A:
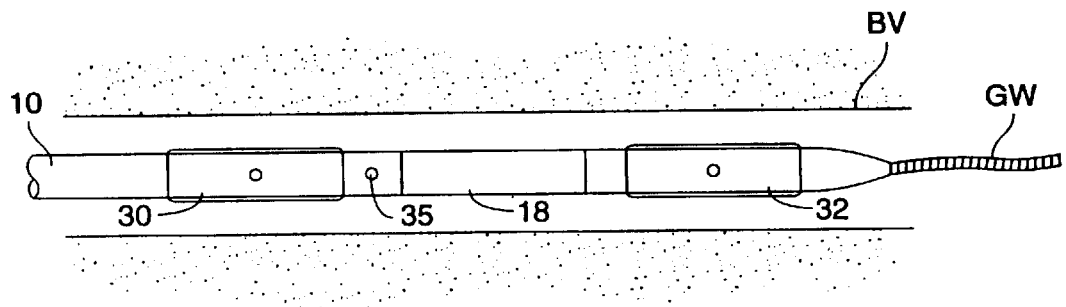
FIGS. 5A–5C illustrate use of the catheter of FIG. 1 in performing nucleic acid transfection within a blood vessel.
Figure 5B:
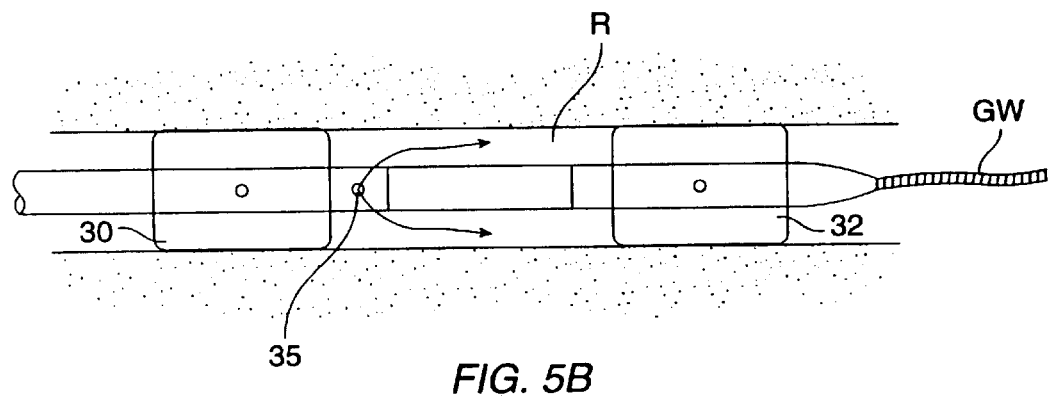
Figure 5C:
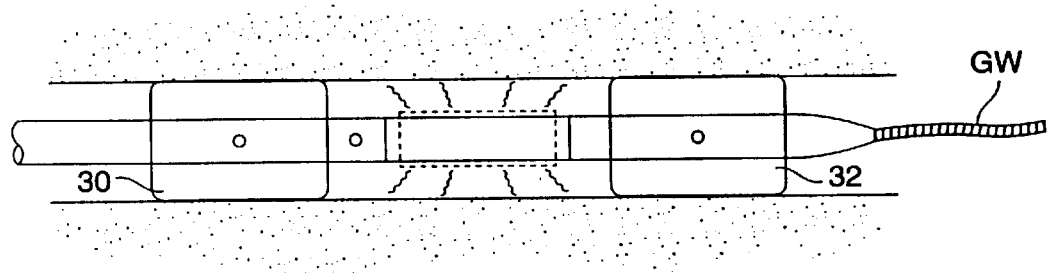

Catheter 10 may be used to deliver nucleic acids to a target region within a blood vessel BV, as illustrated in FIGS. 5A–5C. The catheter 10 is intravascularly introduced to the target region in a conventional manner. Once at the desired target region, as shown in FIG. 5A, the balloons 30 and 32 will be inflated, as illustrated in FIG. 5B, to define an isolated region R within the blood vessel lumen. A suitable liquid medium containing the nucleic acids to be delivered can then be introduced via port 34 and orifice 35 into the isolated region R until a desired concentration of the nucleic acid is achieved. Optionally, the nucleic acid may be replenished and/or recirculated within the region if desired. After sufficient nucleic acid has been introduced, the vibrating interface surface 18 is actuated in order to transmit ultrasonic energy through the medium into the blood vessel wall to enhance uptake of the nucleic acids, as illustrated in FIG. 5C. The vibrational energy is delivered within the frequency ranges and at the intensities described above, typically for periods of time from 10 sec. to 10 min., usually from 20 sec. to 3 min.

Figure 6:
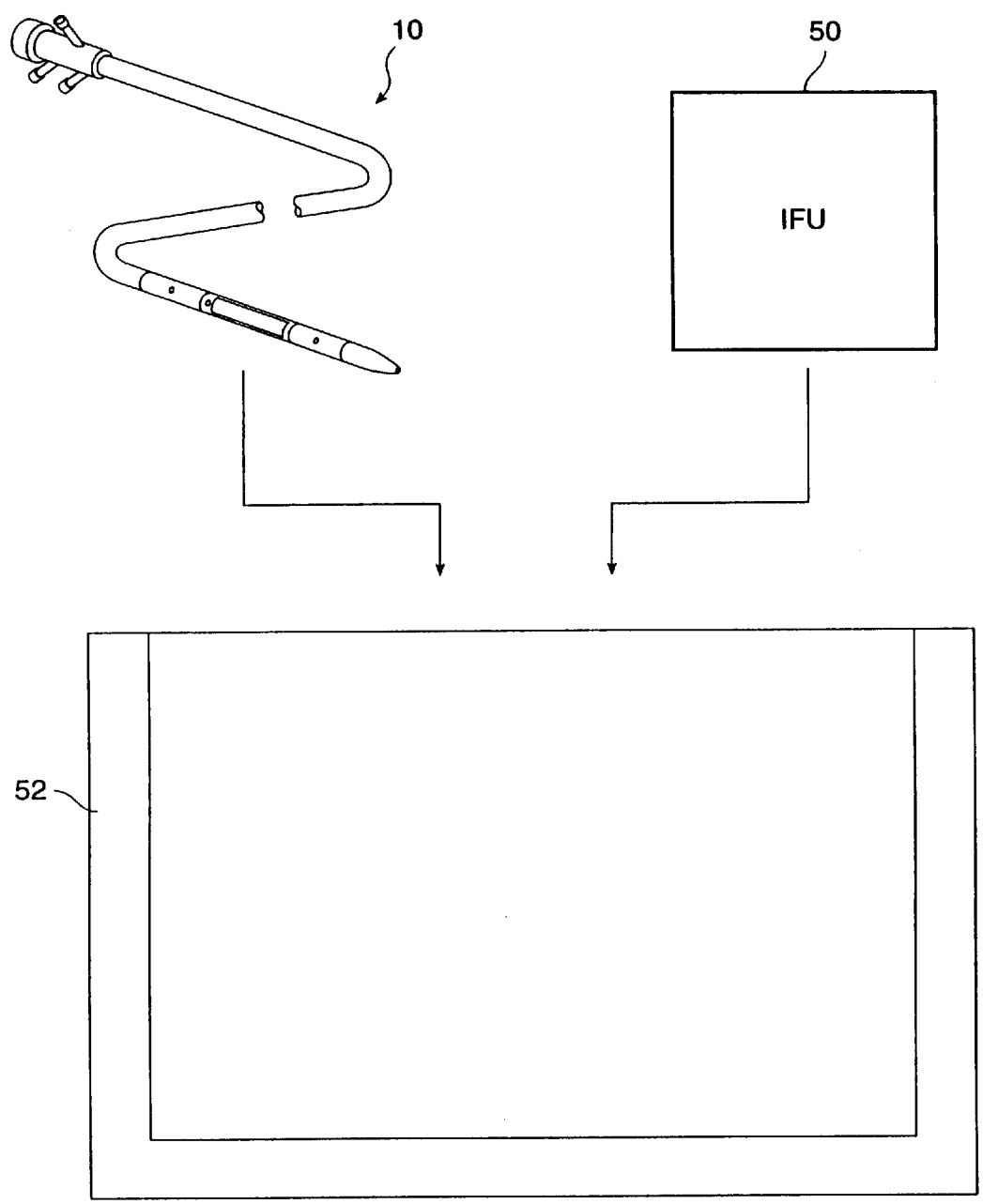
FIG. 6 illustrates a kit constructed in accordance with the principles of the present invention.

Referring now to FIG. 6, the catheters 10 of the present invention will usually be packaged in kits. In addition to the catheter 10, such kits will include at least instructions for use 50 (IFU). The catheter and instructions for use will usually be packaged together within a single enclosure, such as a pouch, tray, box, tube, or the like 52. At least some of the components may be sterilized within the container. Instructions for use 50 will set forth any of the methods described above.

The following examples are offered by way of illustration, not by way of limitation.

EXPERIMENTAL

1. Methods

A. Cell Culture

Explant-derived porcine medial vascular smooth muscle cells (VSMCs) and enzyme-dispersed luminal endothelial cells (ECs) were obtained from the thoracic aorta of Yorkshire White cross pigs aged under 6 months and cultured on gelatin-coated tissue culture flasks (Costar) in Dulbecco's Modified Eagle Medium (DMEM) containing 10% porcine serum; EC cultures were supplemented with EC growth factor (20 µg/ml; Sigma) and heparin (90 µg/ml; Sigma).

B. Transfection Conditions

All transfections were for 3 h at 37° C. in 24-well plates with cells at 60–70% confluence, and were stopped by dilution with 1 ml of fresh culture medium. Naked DNA transfections were carried out in 200 µl DMEM containing 10% porcine serum and 7.5 µg/ml luciferase plasmid DNA (pGL3, Promega) per well. Lipofections were carried out using Promega Tfx-50 (which contains DOPE), according to conditions optimized for VSMCs (200 µl DMEM containing 10% porcine serum; DNA:lipid charge ratio of 4:1; 7.5 µg/ml final DNA concentration) and ECs (200 µl serum-free DMEM; DNA:lipid charge ration 3:1; 5 µg/ml final DNA concentration).

Where applicable, ultrasound exposure (USE) was performed 30 min. into the transfection period using a 10 mm diameter air-backed piezoelectric flat plate ceramic transducer activated to produce continuous wave (CW) 1 MHz ultrasound at 0.4 W/cm$^2$ using a multifunctional signal generator (DS 345, Stanford Research Systems) working through a Krohn-Hite 7500 power amplifier, monitored continuously using an oscilloscope (TDS 220, Tektronix). The 24-well plates were suspended in a 2 cm-deep polystyrene water bath at 37° C. during USE, which was performed for 60 s with the transducer within the transfection medium 2 mm above the cell monolayer. This level of USE caused only minor acute damage to the cell monolayer and had no effect on naked or liposome-complexed plasmid DNA integrity as accessed by agarose gel electrophoresis (data not shown). Temperature was recorded continuously using a custom-built computerized probe placed adjacent to the ultrasound transducer. A 10 mm diameter heating probe was constructed in-house and used to mimic the rate of rise and final temperature achieved during USE.

C. Assays for Luciferase Activity, Adherent Cell Number and Validity

Luciferase activity in VSMC and EC lysates 48 h after transfection was measured using the GenGlow kit and 1253 Luminometer (BioOrbit) and expressed as light units per microgram total cell protein (assayed in parallel using the Bradford method (BioRad)). Parallel wells were trypsinised at 0, 3, 18 and 48 h after treatment. Cell counts and viability were assayed by Coulter™ counter and FACS analysis of propidium-iodide and fluorescein diacetate exclusion.

D. Time Lapse Video Microscopy (TLVM)

Identically seeded subconfluent VSMCs in 24-well plates were observed by TLVM using a Leitz DM 1RB inverted microscope (Leica UK Ltd) within a 37° C. environment chamber. One frame of a high-power field was recorded every 2.4 min. at for 48 h beginning 3 h after USE (where applicable) using a monochrome video camera (Sony), Super-VHS video recorder (Panasonic) and a BAC900 animation controller (EOS electronics AV Ltd, Barry, UK). A mitotic event was recorded when 2 daughter cells appeared from a single dividing cell. An apoptotic event was recorded when an individual cell underwent the typical morphological changes of membrane blebbing, cytoplasmic shrinkage, nuclear condensation and dislodgement.

E. Statistical Analysis

All data are presented as mean ±SEM. Treatments were compared using the Friedman ANOVA test, and the Wilcoxon signed rank test for post hoc comparisons. Values were considered to be significantly different if $p<0.05$, applying the Bonferroni correction for multiple comparisons were appropriate. The n numbers quoted refer to the number of separate experiments; on each occasion each treatment was performed in triplicate wells.

2. Results

Figure 7:
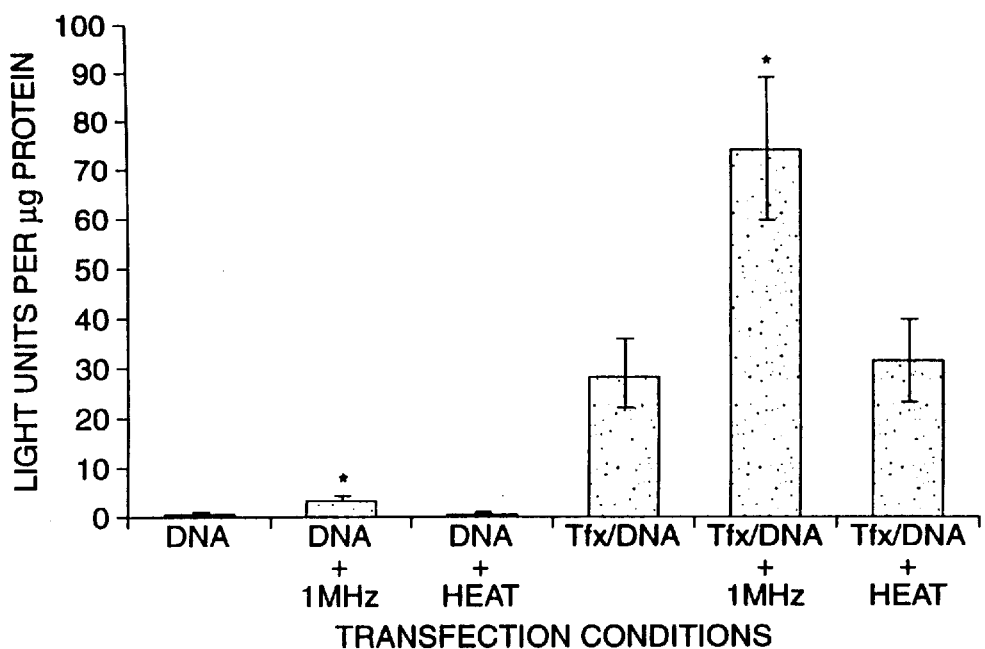
FIGS. 7–10 are charts and graphs comparing transfection according to the present invention with controls. Porcine VSMCs (FIGS. 7 and 9) and ECs (FIGS. 8 and 10) were transfected for 3 h with naked or liposome (Promega Tfx-50) complexed luciferase DNA (n=12) and luciferase activity in cell lysates was determined after 48 h at 37° C.

Luciferase activity was barely detectable in VSMC lysates 48 h after transfection with naked plasmid alone (0.4±0.2 LU/µg), but was 7.5-fold higher in parallel wells exposed to 1 MHz ultrasound (3.0±2.0 LU/µg; n=12; $p<0.02$ cf naked DNA alone), equivalent to 11% of that achieved following optimal lipofection alone (27.6±6.9 LU/µg) (FIG. 7). USE during lipofection further enhanced reporter gene expression, by almost 3-fold (72.8±17 LU/µg; n=12; $p<0.002$ cf lipofection alone) (FIG. 7). The temperature of the culture medium increased progressively during USE, reaching 14±1° C. above baseline after 60 s. To exclude the possibility that ultrasound-induced heating may be responsible for the observed effects on reporter gene expression, VSMCs were exposed to an identical rate and final temperature rise over 60 s in the absence of 1 MHz ultrasound. No effect on luciferase activity in VSMC lysates after 48 h was observed (FIG. 7).

Figure 8:
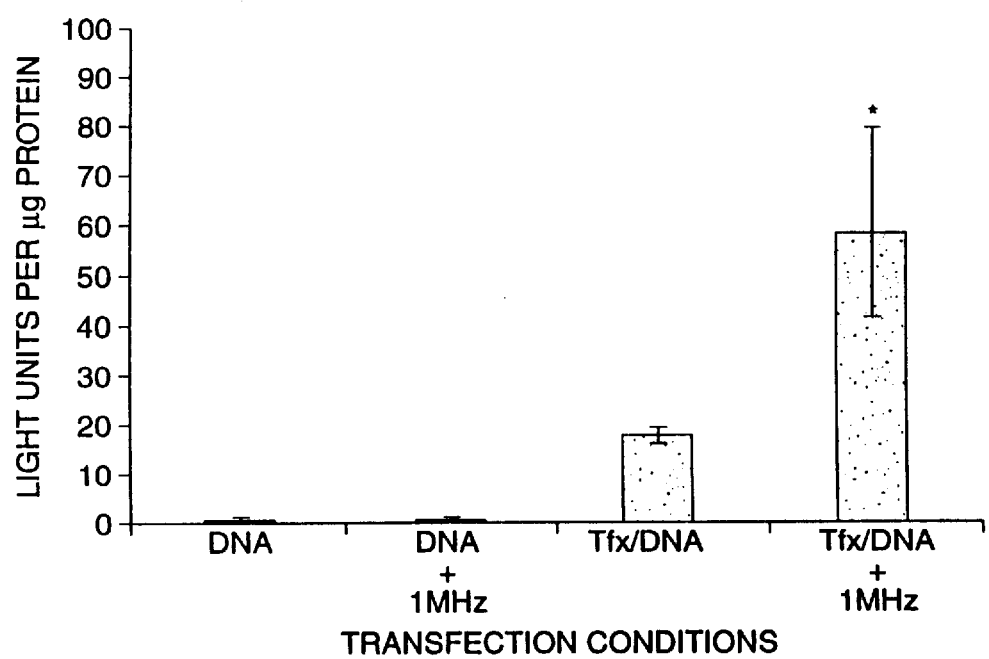

Luciferase activity was almost undetectable in EC lysates 48 h after transfection with naked DNA (0.7±0.1 LU/µg) but, in contrast to the results with VSMCs, was not enhanced by adjunctive USE; (1.2±0.2 LU/µg; n=4; p=NS of naked DNA alone) (FIG. 8). USE during lipofection, however, enhanced reporter gene expression in ECs by more than 3-fold, from 17.7±1.1 to 57.8±20.2 LU/µg (n=4; $p<0.04$).

Figure 9:
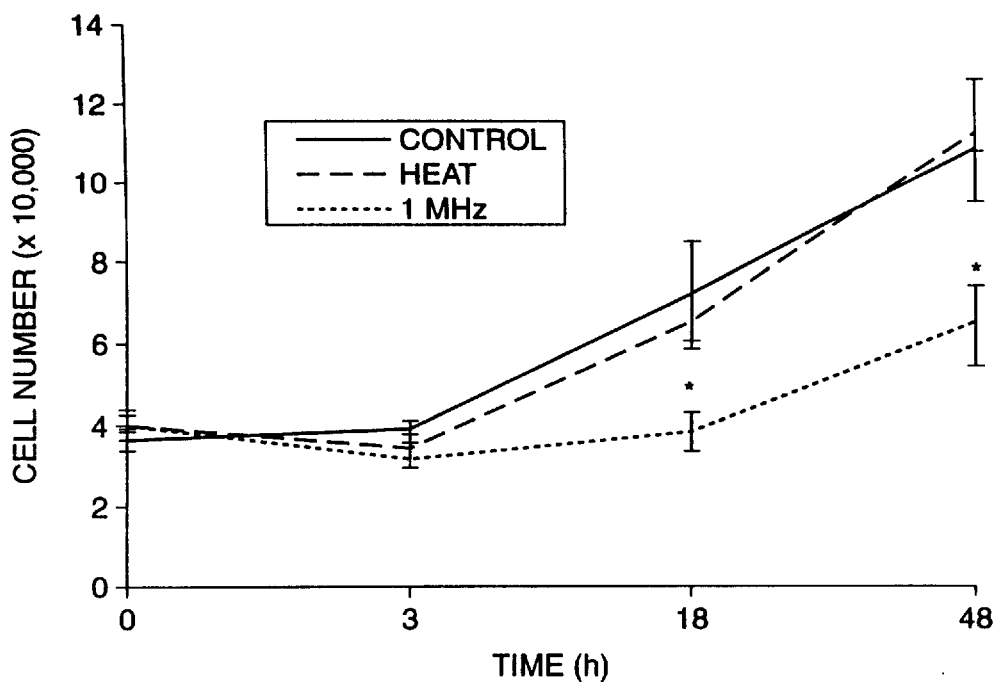
Figure 10:
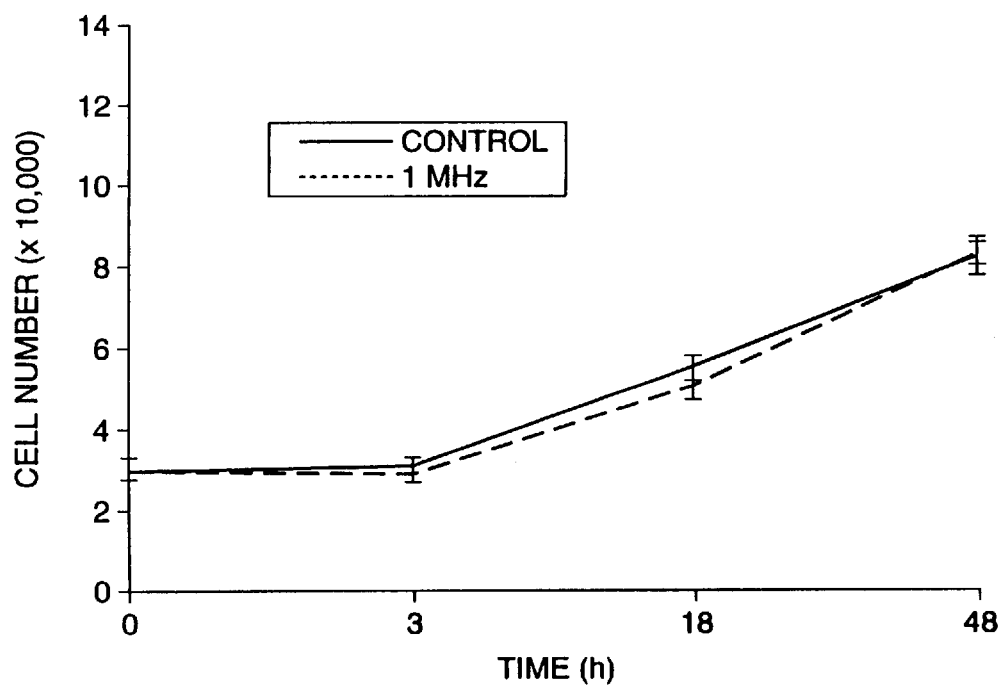
Figure 11:
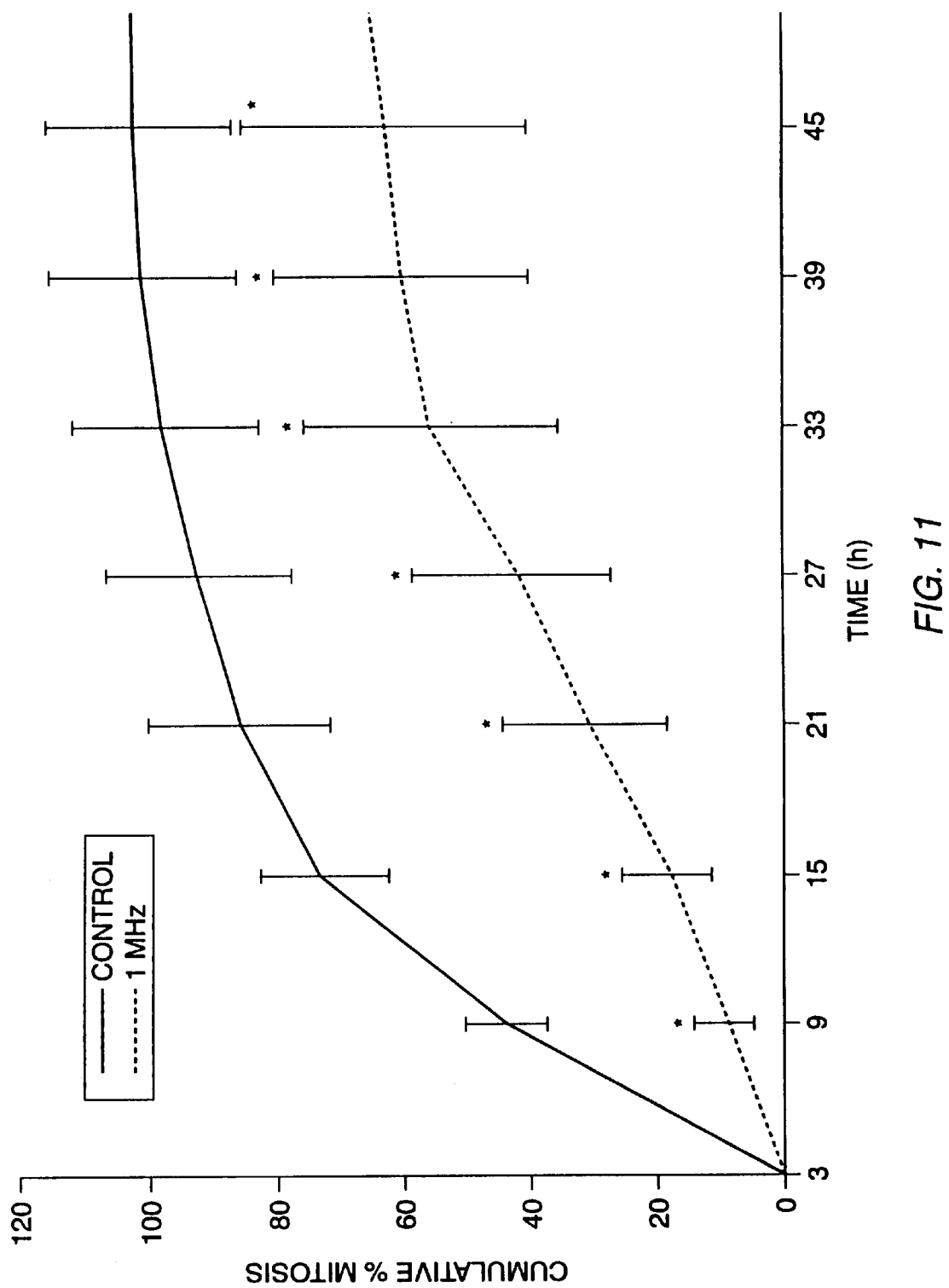
FIG. 11 compares cumulative mitosis in two wells of subconfluent porcine VSMCs which were observed concurrently by TLVM for 48 h and the cumulative rate of mitosis was analyzed (n=3). One well was exposed to ultrasound (1 MHz, CW, 0.4 W/cm$^2$, 60 s) prior to filming. Asterisks indicate significant differences between control and ultrasound-exposed cells ($p<0.05$).

USE had no significant effect on adherent cell number at 3 h but was associated with much smaller subsequent increases compared with either untreated control wells or those exposed to a temperature rise alone (FIG. 9). This effect was not observed in ultrasound-exposed EC, which increased in number in identical fashion to control cells (FIG. 10). Adherent VSMC and EC viability was identical in control, heat-exposed and 1 MHz-treated wells and remained unchanged throughout (p=NS for each treatment and at all timepoints, data not shown). We did not observe an excess of detached VSMCs in the culture medium following USE, either by eye or by performing cell counts on the culture medium itself (data not shown). TVLM analysis of identically prepared, randomly cycling, subconfluent VSMCs showed that ultrasound exposure significantly reduced the rate of mitosis (FIG. 11). In contrast, ultrasound had no effect on the rate of apoptosis in the same cultures (cumulative percent apoptosis in control wells; 9.9±4.2% at 24 h, 11.6±5.0% at 48 h. In ultrasound-exposed wells; 4.8±4.3% a 24 h, 7.6±5.2% at 48 h; n=3; p=NS for all comparisons).

3. Discussion

In the present study we demonstrate that adjunctive USE enhances reporter gene expression following optimal naked DNA and/or lipofection of primary vascular smooth muscle cells. A number of recent reports have shown that ultrasound also enhances reporter gene expression following transfection of non-vascular, mainly immortalized, cells in vitro, including human prostate cancer (Tata et al. (1997) Biochem. Biophys. Res. Comm. 234:64–67), chondrocyte (Greenleaf et al. (1998) Ultrasound Med. Biol. 24:587–595), Chinese Hamster Ovary (Bao et al. (1997) Ultrasound Med. Biol. 23:953–959), and HeLa cell lines (Unger et al. (1997) Invest. Radiol. 32:723–727), primary rat fibroblasts and chondrocytes (Kim et al. (1996) Hum. Gene. Ther. 7:1339–1346), and mouse NIH/3T3 and mammary tumor cell lines (Unger et al. (1997) Invest. Radiol. 32:723–727). Transfection rates of up to 15% of surviving immortalized human chondrocytes using naked DNA have been reported following exposure to CW 1 MHz ultrasound, and two to 1000-fold enhancements in lipofection efficiency have been reported in a number of immortalized cell lines, in each case independent of heat. The three to 7.5-fold enhancements recorded herein probably underestimate the effects of ultrasound for several reasons. First, USE was performed from above to minimize standing wave formation resulting from reflection at fluid/air and plastic/air interfaces. This constrained transducer design such that only one-third of each cell monolayer was covered by the transducer. Secondly, the choice of ultrasound parameters may not have been optimal. We used 1 MHz ultrasound at less than 1 W/cm$^2$ as this corresponds to the mean output of diagnostic transducers and is clinically safe (Henderson et al. (1995) Ultrasound Med. Biol. 21:699–705; Barnett et al. (1996) Ultrasound Med. Biol. 24:i–xv, S1–58). Furthermore, USE at this level had no effect on DNA integrity or vascular cell viability in vitro. Additionally, the small number of cells physically dislodged acutely during USE may have been those most likely to have been transfected. These cells were lost to analysis under these tissue culture conditions, although this situation may not pertain to VSMCs and ECs within the intact vessel wall in vivo.

Low intensity ultrasound requires pre-formed microbubbles or nucleation sites to generate cavitation, and these conditions certainly exist in the non-degassed culture media used in our experiments. The effects of ultrasound in vitro may be further enhanced in the presence of additional microbubbles in the form of the echocontrast agent Albunex™, and naked DNA transfection rates approaching those achieved with lipofection have been reported (Tata et al. (1997) Biochem. Biophys. Res. Comm. 234:64–67). There is relatively little evidence for the existence of microbubbles or cavitation nuclei, however, in blood. Thus, methods according to the present invention which combine low intensity USE and local delivery of DNA mixed with (or even within) microbubbles would be useful not only to focus but also restrict gene delivery to a desired target site in a blood vessel.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for transfecting vascular smooth muscle cells, said method comprising:

exposing viable smooth muscle cells in vitro to nucleic acids adapted to transfect vascular smooth muscle cells;

exposing the viable smooth muscle cells to vibratory energy at a frequency and intensity selected to enhance nucleic acid uptake by and transfection of the smooth muscle cells.

2. A method for preferentially transfecting vascular smooth muscle cells in a population of vascular smooth muscle cells and vascular endothelial cells, said method comprising:

exposing the cell population in vitro to nucleic acids adapted to transfect vascular smooth muscle cells; and exposing the cell population to vibratory energy at a frequency and intensity selected to enhance nucleic acid uptake by and transfection of the nucleic acids by the smooth muscle cells.

3. A method as in any of claims 1 to 2, wherein the vibratory energy is at a frequency in the range from 1 kHz to 10 MHz.

4. A method as in any of claims 1 to 2, wherein the vibratory energy has an intensity in the range from 0.01 W/cm$^2$ to 100 W/cm$^2$.

5. A method as in claim 4, wherein the vibratory energy is delivered with a duty cycle in the range from 1% to 100%.

6. A method as in any of claims 1 to 2, wherein the vibratory energy is applied at a frequency in the range from 1 kHz to 10 MHz and an intensity in the range from 0.01 W/cm$^2$ to 100 W/cm$^2$.

7. A method as in claim 5, wherein the vibratory energy is applied for a cumulative treatment time in the range from 10 seconds to 900 seconds.

8. A method as in claim 5, wherein the vibratory energy is applied with a duty cycle in the range from 1% to 100%.

9. A method as in any of claims 1 to 2, wherein the nucleic acids are selected from the group consisting of genes, gene fragments, sense polynucleotides, anti-sense polynucleotides, and oligonucleotides.

10. A method as in any of claims 1 to 2, wherein the nucleic acids encode an angiogenic factor endothelial nitric oxide synthase, tissue inhibitor of metalloproteinases, or proto-oncogene protein p21.

11. A method as in any of claims 1 to 2, further comprising introducing a medium comprising cavitation nucleii together with the nucleic acids.

12. A method as in claim 11, wherein the nucleic acids are delivered to the blood vessel together with the medium containing cavitation nuclei.

13. A method as in claim 12, wherein the cavitation nucleii are microbubbles.

* * * * *